United States Patent
Lu et al.

(10) Patent No.: US 8,000,940 B2
(45) Date of Patent: Aug. 16, 2011

(54) SHAPE PARAMETER FOR HEMATOLOGY INSTRUMENTS

(75) Inventors: Jiuliu Lu, Homestead, FL (US); Phaisit Chewputtanagul, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 371 days.

(21) Appl. No.: 12/247,650

(22) Filed: Oct. 8, 2008

(65) Prior Publication Data
US 2010/0088066 A1    Apr. 8, 2010

(51) Int. Cl.
*G06F 19/00* (2011.01)
*G06F 17/40* (2006.01)

(52) U.S. Cl. ........... 702/189; 702/187

(58) Field of Classification Search ........ 702/1, 127, 702/179, 180, 187, 189
See application file for complete search history.

(56) References Cited

U.S. PATENT DOCUMENTS

| | | | | |
|---|---|---|---|---|
| 2,965,300 | A * | 12/1960 | Radley et al. | 708/806 |
| 3,146,344 | A * | 8/1964 | Palmer | 702/179 |
| 4,661,913 | A * | 4/1987 | Wu et al. | 702/19 |
| 7,471,393 | B2 * | 12/2008 | Trainer | 356/336 |
| 2004/0010375 | A1 | 1/2004 | Schomacker et al. | |
| 2004/0206913 | A1 | 10/2004 | Costa et al. | |
| 2007/0020697 | A1 | 1/2007 | Cualing et al. | |
| 2007/0165225 | A1 * | 7/2007 | Trainer | 356/335 |
| 2007/0248265 | A1 | 10/2007 | Lundstrom et al. | |
| 2007/0250548 | A1 | 10/2007 | Huo et al. | |
| 2008/0108101 | A1 | 5/2008 | Miyazaki | |
| 2010/0110103 | A1 * | 5/2010 | Ramirez et al. | 345/619 |

FOREIGN PATENT DOCUMENTS
WO  WO 2005/114191 A2   12/2005

OTHER PUBLICATIONS
International Search Report for Appl. No. PCT/US09/52125, mailed Sep. 15, 2009, 4 pgs.

* cited by examiner

*Primary Examiner* — Edward R Cosimano
(74) *Attorney, Agent, or Firm* — K & L Gates LLP; Louis C. Cullman; Dean G. Stathakis

(57) ABSTRACT

Systems, methods, and computer program products are provided for describing characteristics of a data sample. This description is used to represent the shape of a histogram of the data sample.

32 Claims, 9 Drawing Sheets

SHAPE PARAMETER FOR HEMATOLOGY INSTRUMENTS

BACKGROUND

1. Field

The present invention relates generally to data interpretation and, more specifically, to diagnostic techniques using particle analyzers, such as flow cytometer.

2. Description of the Background Art

Flow cytometry is a technique that is commonly employed to analyze individual particles in a sample in order to detect characteristics of the particles. A flow cytometry device performs analysis on a single particle at a time in order to determine information about the sample, including concentrations, percentages, positional parameters, and shape parameters, among other characteristics.

Hematology instruments commonly implement flow cytometry in order to aid in the detection of abnormalities in a given blood sample. Such abnormalities are often indicative of disease, and therefore it is important that hematology instruments provide consistently useful results.

Various methods can be employed by flow cytometry devices to perform multiparametric analysis of individual particles, such as blood cells in the case of hematology instruments, the results of which are then aggregated to produce the characteristic data for the blood sample. For example, the volume of a cell can be determined indirectly by applying direct current to the cell suspended in a conductive diluent, resulting in a change in electrical resistance based on the volume of the cell. Additional parameters that may be used to interrogate a cell may include conductivity measurements using radio frequencies, as well as light scatter parameters using a laser. The types of measurements that can be used to determine characteristics of cells is constantly expanding as the field continues to evolve, and instruments implementing flow cytometry are improved to generate additional parametric data.

As noted, one of the ways to interpret blood sample characteristics is through the use of shape parameters. Shape parameters are used to characterize the distribution of data on a two-dimensional histogram. A typical method for determining a shape parameter for a blood sample is to determine the standard deviation based on the given measurement data. For example, a population, or sample, of blood cells is tested in a flow cytometry device to generate scalar values representing two features of each individual cell. These two features may be, again for example, the volume and conductivity of the cell. In order to generate data that can be easily used to flag suspect blood samples, the standard deviation of the population is determined based on the aggregate of volume and conductivity data for many cells.

Although standard deviation data for flow cytometry results is often useful in diagnosis, it may have limitations which can hamper effective clinical study. Despite best efforts, data from any instrumentation is prone to noise. This can result in skewing of the calculated standard deviation, deteriorating its usefulness. If two populations have otherwise identical histograms, except the first has an outlier event caused by noise that the second population does not, the standard deviation of the two samples may be significantly different. However, since the two populations have otherwise identical histograms, it would be useful to determine a shape parameter that indicates this similarity.

Moreover, since standard deviation is a scalar value, it cannot capture the intricacies associated with multivariate descriptions of the population characteristics. Two populations having entirely different histograms over two parameters may nevertheless have similar or identical standard deviations.

Accordingly, what is desired is a parameter capable of providing detailed shape information without being significantly impacted by noise.

SUMMARY OF INVENTION

Embodiments of the invention include a method for describing characteristics of a data sample. The method comprises generating a multi-dimensional histogram from data representative of a plurality of physical measurement parameters on a detected object, determining a central portion of the histogram, and computing a shape parameter for the histogram along a slicing line originating at the central portion.

Additional embodiments of the invention include a system for describing characteristics of a data sample. The system comprises a generating module to generate a histogram from data representative of physical measurements on a detected object, a determining module to determine a central portion of the histogram, and a computing module to compute a shape parameter for the histogram along a slicing line originating at the central portion.

Further embodiments of the invention include a computer program product comprising a computer-usable medium having computer program logic recorded thereon for enabling a processor to describe characteristics of a data sample. The computer program logic comprises a generating module configured to enable the processor to generate a histogram from data representative of physical measurements on a detected object, a determining module configured to enable the processor to determine a central portion of the histogram, and a computing module configured to enable the processor to compute a shape parameter for the histogram along a slicing line originating at the central portion.

Other embodiments of the invention include a computer-readable storage medium having computer program code recorded thereon that, when executed by a processor, causes the processor to perform a method for describing characteristics of a data sample. The method comprises generating a histogram from data representative of physical measurements on a detected object, determining a central portion of the histogram, and computing a shape parameter for the histogram along a slicing line originating at the central portion.

Embodiments of the invention also include a method for describing characteristics of a population of blood cells. The method comprises acquiring a blood cell from the population of blood cells in an instrument aperture, obtaining data representative of two physical measurements for the blood cell, determining the population type of the population based on the data, generating a two-dimensional histogram from data, wherein the data is aggregated with additional data corresponding to the population to generate the histogram, determining a central portion of the histogram, and computing a shape parameter for the histogram along a slicing line originating at the central portion.

Added embodiments of the invention include a method for detecting irregularities in a biological sample. The method comprises generating a histogram from data representative of physical measurements on the biological sample, determining a central portion of the histogram, interpolating frequency values for the histogram along a slicing line originating at the central portion, calculating the shape parameter using the interpolated frequency values, creating a plot of the shape parameter against an angle of the slicing line, and comparing the plot to an expected plot.

Moreover, embodiments of the invention include a system comprising a flow chamber, a detector configured to generate electronic signals responsive to particles passing through the flow chamber, a receiver configured to receive the electrical signals and to convert the electrical signals to captured data, and a data processor. The data processor comprises a generating module to generate a histogram from the captured data, a removing module to remove a portion of the histogram having a characteristic below a first threshold value, a smoothing module to smooth a remaining portion of the histogram through removing an additional portion of the remaining portion having a characteristic below a second threshold value, a determining module to determine a central portion of the histogram, and a computing module to compute a shape parameter for the histogram along a slicing line originating at the central portion. The system further comprises a display configured to display a plot of the shape parameter against an angle of the slicing line.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form a part of the specification, illustrate embodiments of the present invention and, together with the description, further serve to explain the principles of the invention and to enable a person skilled in the relevant art to make and use the invention.

Figure 1:
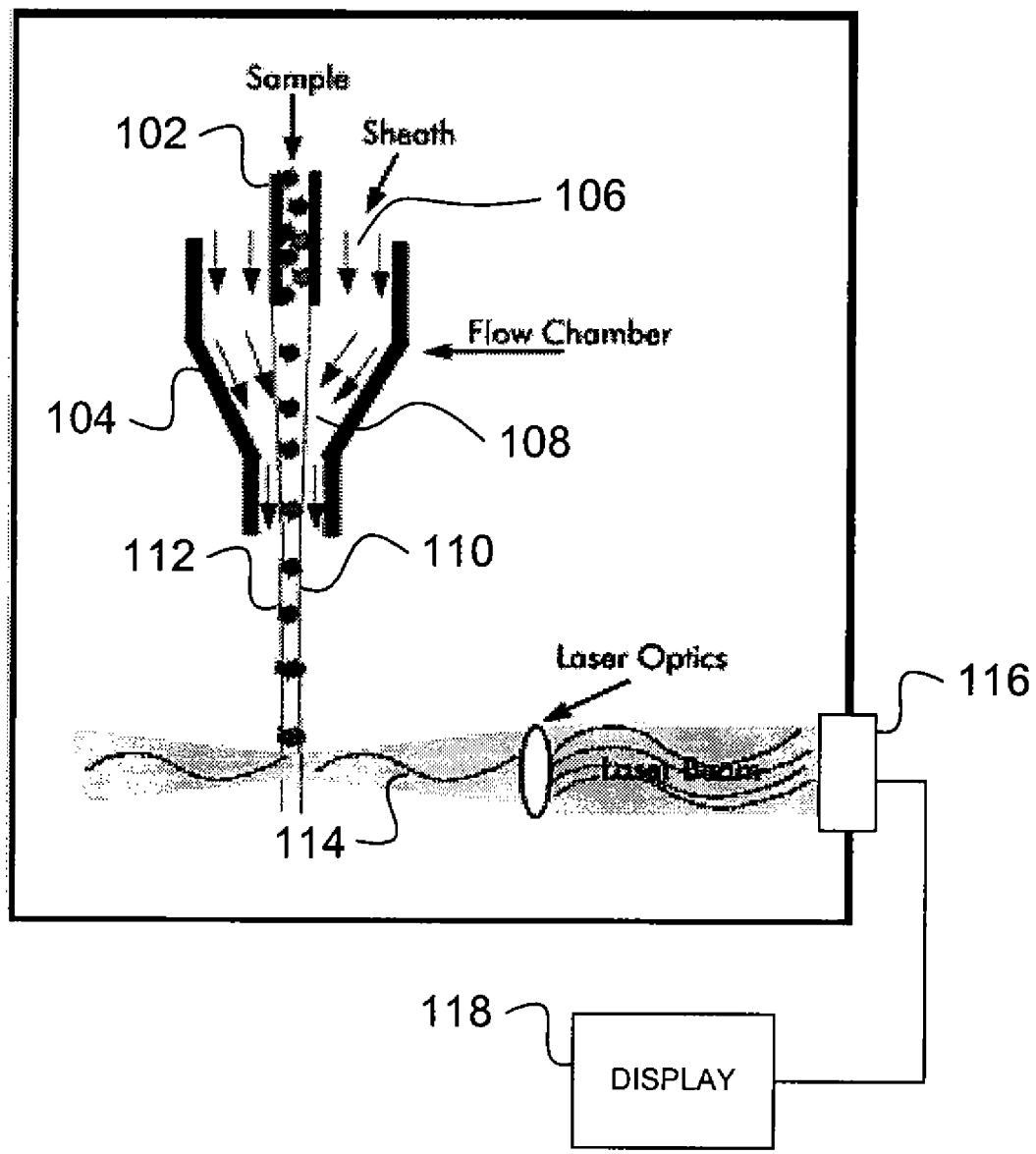
FIG. 1 illustrates an exemplary flow cytometer with which embodiments of the present invention may be used.

The present invention will now be described with reference to the accompanying drawings. In the drawings, generally, like reference numbers indicate identical or functionally similar elements. Additionally, generally, the left-most digit(s) of a reference number identifies the drawing in which the reference number first appears.

DETAILED DESCRIPTION

I. Introduction

The following detailed description of the present invention refers to the accompanying drawings that illustrate exemplary embodiments consistent with this invention. Other embodiments are possible, and modifications can be made to the embodiments within the spirit and scope of the invention. Therefore, the detailed description is not meant to limit the invention. Rather, the scope of the invention is defined by the appended claims.

It would be apparent to one of skill in the art that the present invention, as described below, can be implemented in many different embodiments of software, hardware, firmware, and/or the entities illustrated in the figures. Any actual software code with the specialized control of hardware to implement the present invention is not limiting of the present invention. Thus, the operational behavior of the present invention will be described with the understanding that modifications and variations of the embodiments are possible, given the level of detail presented herein.

Although the techniques described herein are generally described in the context of flow cytometry for hematology studies, it is understood that the concepts can be applied to other areas that involve similar needs for data analysis. Moreover, although the sample typically under study is a blood cell from a sample (or "population") of blood cells, the same techniques can be applied to many different particles to measure their properties. Accordingly, the discussion herein as it relates to flow cytometry and hematology is presented by way of example, and not limitation.

FIG. 1 illustrates the operation of a simplified exemplary flow cytometer 100. Flow cytometry uses the principles of light scattering, light excitation, and emission of fluorochrome molecules to generate specific multi-parameter data from particles and cells. A sample 102 containing particles, such as cells 112, is injected into the center of a sheath flow 106 contained in a flow chamber 104. The combined flow 108 is reduced in diameter, forcing each cell 112 into the center of a stream 110. A beam 114 of light, such as laser light, is directed through stream 110. As the cells 112 enter the beam 114, they scatter light and any fluorochromes present are excited to a higher energy state. The flourochromes' energy is released as a photon of light with specific spectral properties unique to each fluorochrome. Detectors in module 116 (not specifically shown) detect one or both of the scattered and fluorescent light to convert them to electrical pulses or signals. In one example, the signals or pulses can be amplified and/or converted to digital values using module 116.

Thus, flow cytometry data includes a set of values for various parameters for respective cells. In one example, the set of values associated with each cell is termed an "event." For example, the measured parameters include fluorescent energy emitted at particular wavelengths and scatter (e.g., front scatter and side scatter) intensities. Each event can have a number, N, of measured parameter values associated with it, and may be thought of as a point in N dimensional space. In a typical flow cytometer sample, several million events or more are measured and recorded for analysis. Flow cytometry data may be analyzed after the fact (e.g., read from a data file) or it may be analyzed in substantially real-time as a sample is passing through the instrument.

Other methods exist for measuring additional parameters for individual cells in a sample. For example, cells can be suspended in a conductive diluent while passed through the stream 110. Instead of applying a beam 114 of light, a direct current (DC) is applied to the cell 112 and the change in electrical resistance of the stream 110 is measured. Direct current flows around cells, causing the electrical resistance to change in proportion to the size of the cell 112.

An additional method for measuring additional parameters for individual cells in a sample involves the application of high radio frequency current (RF) to the cell 112. Unlike the direct current application, RF also penetrates the cell membrane, and therefore passes both around and through the cell 112. As a result, a conductivity measurement is obtained, which is a function of both cell volume and internal composition of the cell 112. Conductivity measurements provide information on cellular granularity, nuclear composition, nucleus to cytoplasm ratio, and the chemical composition of the cell 112.

Moreover, it is possible to refine the conductivity measurements determined from the application of DC and RF in order to yield an opacity measurement. Opacity is derived from the ratio of the RF and DC information, which has the effect of removing the volume information to yield an opacity measurement to more closely reflect the internal characteristics of the cell 112.

It is understood that additional techniques may be used, and the aforementioned techniques are provided by way of example, and not limitation. The data used in the applications disclosed herein may be derived from a number of sources, either by direct measurement or, as in the case of opacity above, by deriving the data from other data sources.

Each of the aforementioned techniques generate N parameters per event. By plotting events for a population together, an N-dimensional histogram is created. By comparing this histogram to expected histograms for similar populations, abnormalities in the population can potentially be detected. A module 116 for collecting and analyzing the data generated by flow cytometer 100 is coupled to the flow cytometer 100, in accordance with an embodiment of the present invention, and includes functionality for generating and analyzing the histogram. Module 116 may optionally be located separately from flow cytometer 100, enabling a medical technologist to continue using the flow cytometer 100 for additional study while module 116 processes the data. When this is done, the detectors and other sensing devices are found separately from module 116. In one example, a display 118 is connected to module 116 for displaying the results of the analyzed data, in accordance with a further embodiment of the present invention.

II. Data Gathering and Analysis

Figure 2:
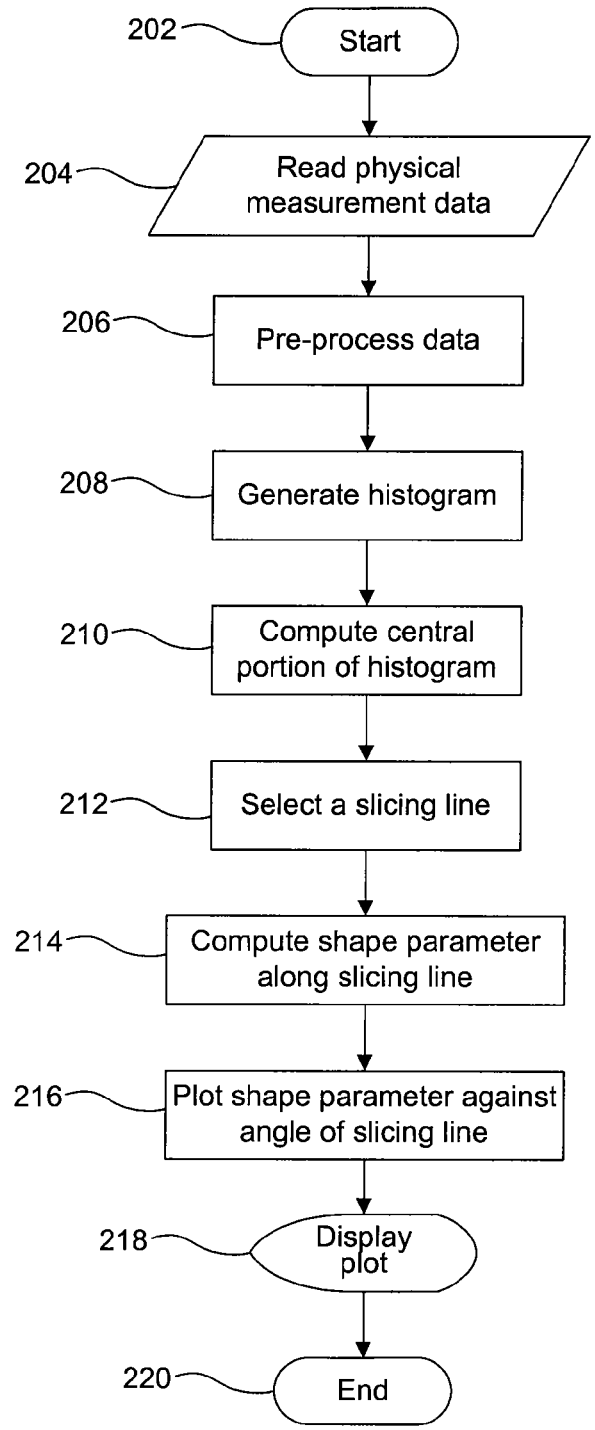
FIG. 2 is a flowchart depicting steps by which data corresponding to events is obtained and analyzed, in accordance with an embodiment of the present invention.

FIG. 2 is a flowchart depicting a method 200 including steps by which data corresponding to events is obtained and analyzed, in accordance with an embodiment of the present invention. This method is performed, in accordance with an embodiment of the present invention, in module 116 of FIG. 1.

Method 200 begins at step 202 and proceeds to step 204, where physical measurement data is obtained. The physical measurement data is obtained for a particular event, the event having N parameters associated with it, each corresponding to a different scalar physical measurement. In accordance with an embodiment of the present invention, the event is a single cell passing through a flow cytometer, and the parameters associated with the event are determined through, for example, one of the techniques discussed in Section I. In accordance with a further embodiment of the present invention, physical measurement data associated with a plurality of events is obtained.

It is understood that the physical measurement data of step 202 may actually correspond to any N-dimensional histogram, where each of the N dimensions corresponds to a property associated with each event in the histogram. These properties are not limited to physical measurements conducted on biological samples, and may instead describe, using scalar values, any N characteristics of the events. In accordance with an embodiment of the present invention, N is greater than 1.

At optional step 206, the data obtained at step 204 is pre-processed to eliminate noise events. This is discussed further in Section III.

A histogram corresponding to the data of step 204 is generated at step 208, in accordance with an embodiment of the present invention. It is understood that the generation of a histogram may correspond to varied types of data storage, and does not necessarily involve the display of the data from step 204 on a graphical display in the form of a histogram. In accordance with an additional embodiment of the present invention, a data array representing a histogram is created in the generation step. Moreover, the step of generating a histogram may occur prior to the pre-processing step 206, in accordance with a further embodiment of the present invention.

In accordance with an embodiment of the present invention, a histogram is generated by associating a range of scalar values along each of the N dimensions associated with N parameters measured for a set of events with an N-dimensional shape having an associated frequency value. The frequency value corresponds to the number of events that fall within the shape. In accordance with a further embodiment of the present invention, each event is associated with two parameters, and therefore can be displayed on a two-dimensional plot. A range of values along each of the two dimensions is associated with a pixel on a graphical display, or a similar two-dimensional construct stored in a memory. A frequency value is kept for each pixel, the frequency value associated with the number of events that lie within the ranges associated with the pixel. In accordance with an additional embodiment of the present invention, the frequency is associated with a color or an intensity for display on a graphical display.

With the data represented in a data structure corresponding to a histogram, a central portion of the histogram is determined or computed at step 210. A slicing line is determined at step 212, and a shape parameter determined or computed 214 along the slicing line. At step 216, this shape parameter is optionally plotted against an angle associated with the slicing line. Further discussion of these steps, slicing lines, and shape parameters is found in Section IV.

The results of the plot are optionally displayed at step 218, for example, on display 118 of FIG. 1. Further discussion of the display and interpretation of results is discussed in Section V. The method 200 then ends at step 220.

Figure 3:
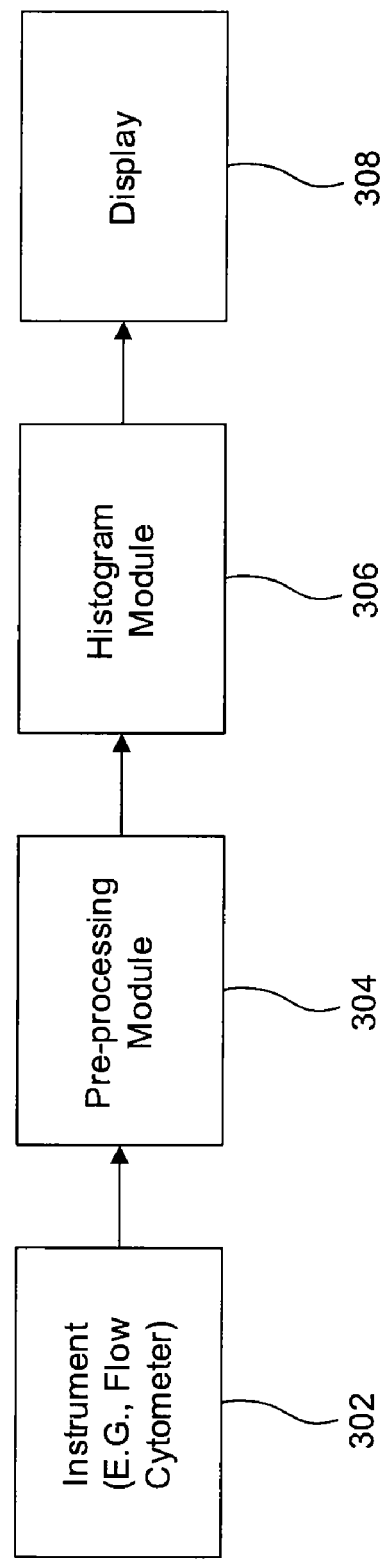
FIG. 3 is a data analysis system in which the method of FIG. 2 can be performed, in accordance with an embodiment of the present invention.

In accordance with a further embodiment of the present invention, the above method can be performed in data analysis system 300 of FIG. 3. The system 300 comprises an instrument 302, such as a flow cytometer, that generates event data. The system 300 may further comprise a pre-processing module 304, which in accordance with an embodiment of the present invention is operable to perform the pre-processing methods disclosed in Section III. Additionally, system 300 comprises a histogram module 306 which is operable to perform the histogram data analysis methods disclosed in Section IV, in accordance with an embodiment of the present invention. A display module 308 is optionally included, in accordance with a further embodiment of the present invention, in order to implement the display and interpretation methods discussed in Section V. The precise delineation of tasks into the four modules of system 300 is presented by way of example, and not limitation, and the methods disclosed throughout this specification can be performed in a single module or any plurality of modules.

III. Pre-Processing of Data Samples to Reduce Noise

Figure 4:
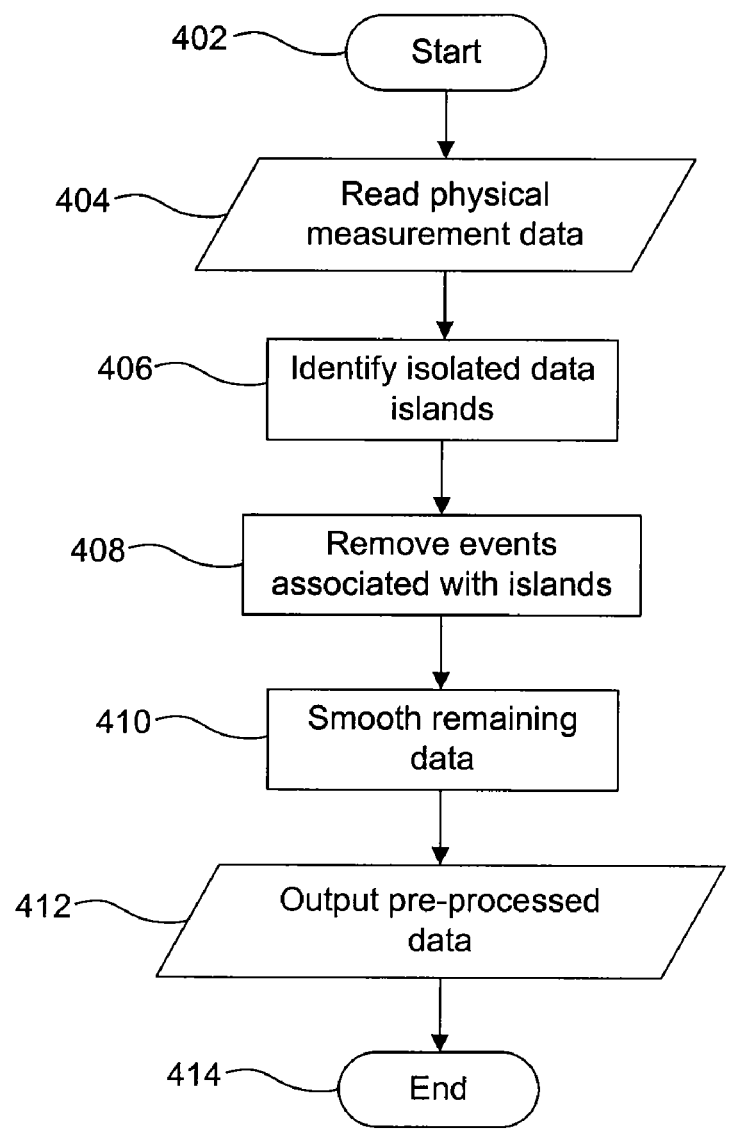
FIG. 4 is a flowchart illustrating steps by which pre-processing is performed on a set of events, in accordance with an embodiment of the present invention.

FIG. 4 is a flowchart depicting a method 400 illustrating steps by which pre-processing is optionally performed on a set of events, in accordance with an embodiment of the present invention. In accordance with a further embodiment of the present invention, the pre-processing steps are performed in a module 304. This module may be integral to an instrument, such as a flow cytometer, producing the data the module is pre-processing, or it may stand alone or be integral to another module or system.

The method 400 begins at step 402, and proceeds to step 404, where physical measurement data is read. In accordance with an embodiment of the present invention, where method 400 is implemented by a stand-alone module, the data of step 404 is read into a local data bank, such as a register, for local processing. In accordance with an additional embodiment of the present invention, the data of step 404 may be read from a data bank shared by a data source, such as a flow cytometer. In accordance with a further embodiment of the present invention, the data being read at step 404 may be transitory in nature, and not physically stored. It is understood that a number of methods for obtaining data for pre-processing by the method of method 400 exist, and the aforementioned methods are presented by way of example, and not limitation.

At step 406, isolated data islands are identified. Isolated data islands are groupings of events which consist of relatively few events and are relatively separated from one or more primary groupings of events, based on some criteria such as, for example, a threshold. At step 408 the events associated with these isolated data islands are removed. Steps 406 and 408 are further discussed below with reference to FIG. 5A. At step 410, the remaining event data is smoothed. Step 410 is further discussed below with reference to FIGS. 5B and 5C.

The resulting pre-processed data is then output at step 412. The output at step 412 is sent to any additional processing modules implementing additional processing steps, such as, for example, histogram module 306 of FIG. 3. The method then ends at step 414.

Figure 5A:
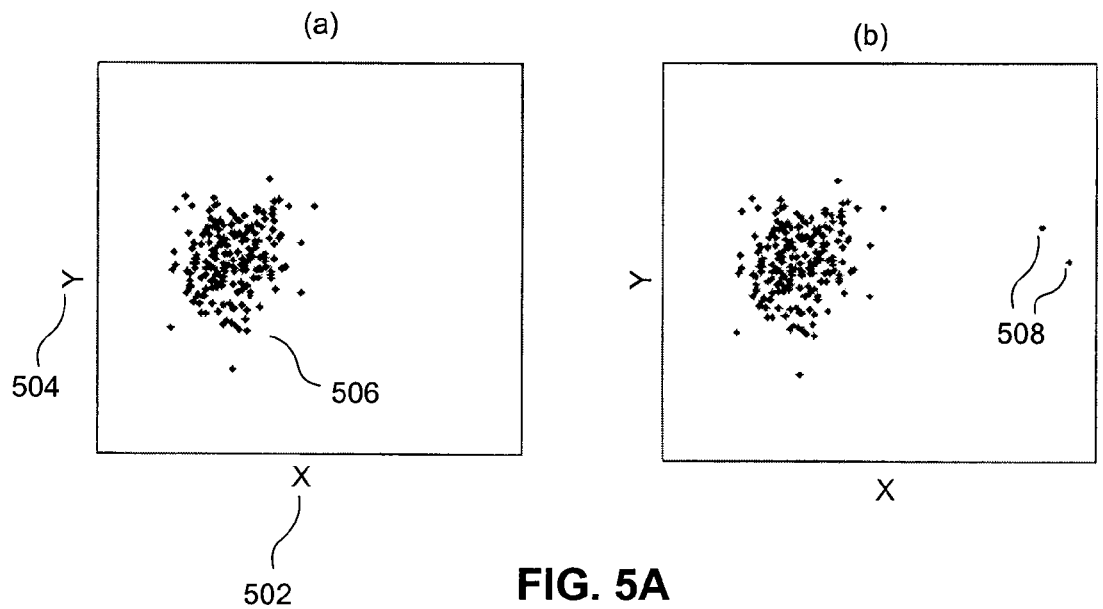
FIG. 5A depicts two scatter plots illustrating a number of events, each event associated with two dimensions, in accordance with an embodiment of the present invention.

FIG. 5A depicts two scatter plots illustrating a number of events, each event associated with two dimensions, in accordance with an embodiment of the present invention. The two dimensions, each corresponding to a parameter of the events, are shown as X 502 and Y 504. Accordingly, an individual event, shown as a point in the scatter plots of FIG. 5A, has an associated X and Y value.

The scatter plot on the left, marked (a), has many events occurring in a grouping 506, the grouping associated with a specific range of values for the X and Y dimensions. The scatter plot on the right, marked (b) has this same grouping 506, but further has two isolated data islands 508 which correspond to events generated by noise. The noise events of islands 508 are generated, in accordance with an embodiment of the present invention, by the instrumentation generating the data shown in the scatter plots of FIG. 5A.

Step 406 of flowchart 400 of FIG. 4 identifies isolated data islands, such as islands 508 of FIG. 5A, and the events associated with the islands are then removed at step 408 from the data set. In order to determine whether one or more events constitute isolated data islands, a number of techniques can be employed, the selection of the technique being interchangeable based on the particular application and the noise characteristics of the data set, in accordance with an embodiment of the present invention. Not all isolated data islands are necessarily caused by noise, so selection of the technique may require consideration of whether noise is the source of any data that may be removed at step 408. In an embodiment, if the number of events within a data region, such as a data region represented graphically by the scatter plots of FIG. 5A within a minimum and maximum X and Y range, is below a certain threshold, then the events in that range are deemed to be isolated data islands. In a further embodiment, if the area occupied within the X and Y dimensions by a set of events is below a certain threshold, then the events in that area are deemed to be isolated data islands. At step 408, any events deemed to be isolated data islands are deleted from the data set.

It is understood that identifying data islands by comparing the area and event count of a set of events to a threshold are just two of a number of techniques that can be employed to identify events caused by noise, and the aforementioned techniques are presented by way of example, and not limitation.

Figures 5B, 5C:
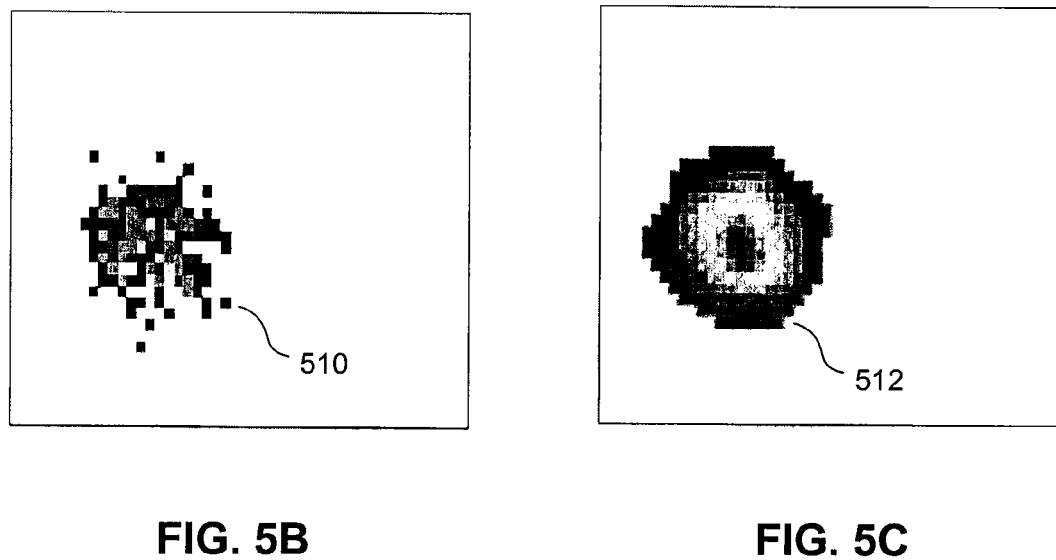
FIG. 5B is a two-dimensional histogram generated from data, such as the event data corresponding to scatter plot (a) of FIG. 5A, in accordance with an embodiment of the present invention.
FIG. 5C is a smoothed histogram corresponding to the histogram of FIG. 5B, in accordance with an embodiment of the present invention.

FIG. 5B is a two-dimensional histogram generated from data, such as the event data corresponding to scatter plot (a) of FIG. 5A. In accordance with an embodiment of the present invention, a histogram is generated by the techniques described in Section II, although it is understood that N-dimensional histograms may be generated by extending the techniques described herein to additional dimensions. The resulting histogram would look, for example, like histogram 510 of FIG. 5B.

Step 410 smoothes the histogram data 510 of FIG. 5B to generate histogram 512 of FIG. 5C. This step eliminates noise in the major event population and presents a histogram that is easier to visually compare to histograms for similar samples, in accordance with an embodiment of the present invention. In accordance with a further embodiment of the present invention, the histogram is smoothed by convolving the histogram with a smoothing kernel, k. In accordance with an additional embodiment of the present invention, k is a Gaussian kernel.

In accordance with yet a further embodiment of the present invention, k is of the form:

$$k = \begin{bmatrix} \frac{1}{16} & \frac{2}{16} & \frac{1}{16} \\ \frac{2}{16} & \frac{4}{16} & \frac{2}{16} \\ \frac{1}{16} & \frac{2}{16} & \frac{1}{16} \end{bmatrix}$$

It is understood that the kernel k can be of a number of forms, and the aforementioned kernels are provided by way of example, and not limitation.

IV. Computing a New Shape Parameter

Figure 6:
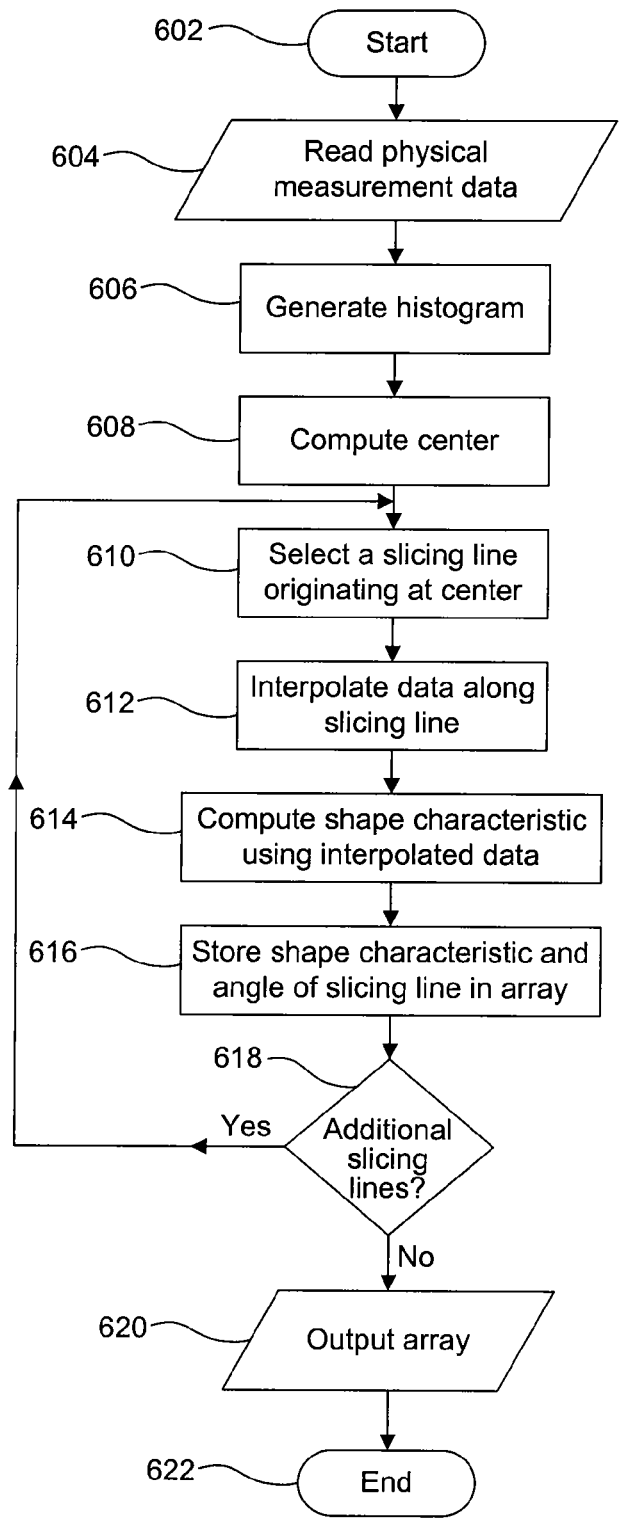
FIG. 6 is a flowchart illustrating steps by which an improved shape parameter is calculated in order to more easily and accurately compare sets of events, in accordance with an embodiment of the present invention.

FIG. 6 illustrates a flowchart depicting a method 600 including steps by which an improved shape parameter is calculated in order to more easily and accurately compare sets of events, in accordance with an embodiment of the present invention. In accordance with a further embodiment of the present invention, the steps of flowchart 600 are performed in a module 306 of FIG. 3. This module may be integral to an instrument, such as a flow cytometer, or it may stand alone or be integral to another module or system.

The method 600 begins at step 602, and proceeds to step 604, where physical measurement data is read. The data may be obtained from a variety of sources including, but not limited to, pre-processing module 304 of FIG. 3, or directly from an instrument, such as a flow cytometer.

At step 606, a histogram is generated from the physical measurement data, in accordance with an embodiment of the present invention. In an additional embodiment of the present invention, the histogram is generated elsewhere and is received as the data received at step 604. The methods by which a histogram may be generated, by way of example, are provided in Section II.

Figure 7A:
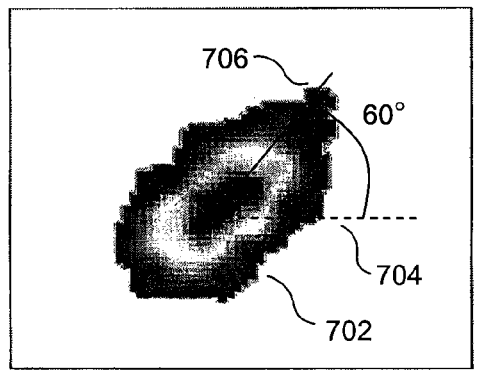
FIG. 7A is an example two-dimensional histogram, in accordance with an embodiment of the present invention.

With the histogram available, a central portion, or center, of the histogram is determined or computed at step 608. With reference to FIG. 7A, the center of the histogram 702 is shown as the mean center point of the event frequencies along the two dimensions. In a two-dimensional histogram, the center point corresponds to an individual pixel or other two dimensional shape, into which the histogram is segmented, in accordance with an embodiment of the present invention.

The center may be calculated using many varied techniques, including the use of the mean, mode, median, or other property of the event population represented by the histogram, and the aforementioned techniques are presented by way of example, and not limitation.

With a center computed, the method proceeds to step 610, where a slicing line is selected. In an embodiment, the slicing line originates at the center. In an additional embodiment, the slicing line originates at some additional point used as the slicing line origin, although further discussion will refer to the center as the origin. The slicing line is a construct that defines a section of the histogram to be analyzed, the analysis for computing a shape parameter along the slicing line, as further discussed herein.

Figure 7B:
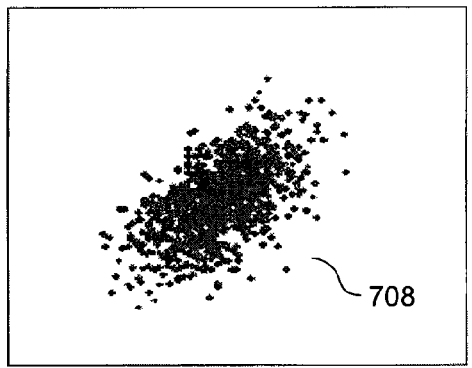
FIG. 7B is an example two-dimensional scatter plot corresponding to the histogram of FIG. 7A, in accordance with an embodiment of the present invention.

For example, the slicing line 706 of FIG. 7A may be used. The direction of any given slicing line is defined as an angle relative to a reference slicing line, also originating at the center, the reference slicing line being selected to represent an angle of zero degrees or radians, in accordance with an embodiment of the present invention. It is understood that the definition of a corresponding angle measurement for the reference slicing line is for purposes of discussion, and any reference slicing line may be used. In FIG. 7A, this reference slicing line is shown as slicing line 704. The angle of slicing line 706 is therefore the angle between the zero degree reference slicing line and slicing line 706, or 60° in the example of FIG. 7A. A scatter plot 708 corresponding to the histogram 702 of FIG. 7A is shown at FIG. 7B for reference.

Following the slicing line, the histogram is interpolated along the slicing line at step 612 to determine or calculate a profile along the slicing line, in accordance with an embodiment of the present invention. This results in the creation of a one-dimensional histogram corresponding to the profile. It is understood that a similar technique can be employed for any N-dimensional histogram, where N is greater than 1, such that an N−1-dimensional profile is determined along a slicing N−1-dimensional shape, such as a two-dimensional profile along a slicing plane in a three-dimensional histogram. The use of a two-dimensional histogram is by way of example, and not limitation.

With a histogram corresponding to the profile determined, a shape characteristic is then determined at step 614. The shape characteristic is a scalar value, which can be determined using a variety of techniques. For example, the standard deviation can be calculated on the one-dimensional histogram, resulting in a useful shape parameter along the slicing line. Additional techniques involve the calculation of a mean along the slicing line and determining or calculating a distance along the slicing line beyond which values drop below a threshold, although any technique resulting in a shape characteristic along the slicing line may be used. Typically, the shape characteristic provides some distinguishing information regarding features of the one-dimensional histogram which it purports to represent.

Having computed a shape characteristic along a slicing line, the slicing line being associated with an angle relative to a reference slicing line, the shape characteristic and angle are stored together in a data structure. In accordance with an embodiment of the present invention, the shape characteristic and angle are stored in an array at step 616.

At step 618, a determination is made as to whether additional slicing lines should be processed. In accordance with an embodiment of the present invention, a set of slicing lines evenly-distributed through $2\pi$ radian (360°) space relative to a 0° reference slicing line is used, although other mechanisms for selecting slicing lines may be employed. If additional slicing lines remain to be processed, then the method returns to step 610. Otherwise, the computed data, including angles of the slicing lines associated with the shape characteristics, are output at step 620, in accordance with an embodiment of the present invention. The method ends at step 622.

V. Shape Parameter Analysis

Figure 7C:
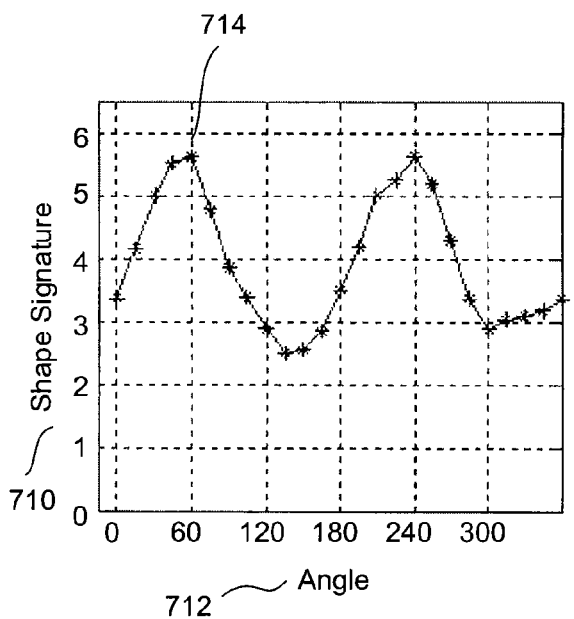
FIG. 7C is an X-Y plot of computed shape characteristics to slicing angles, in accordance with an embodiment of the present invention.
Figure 7D:
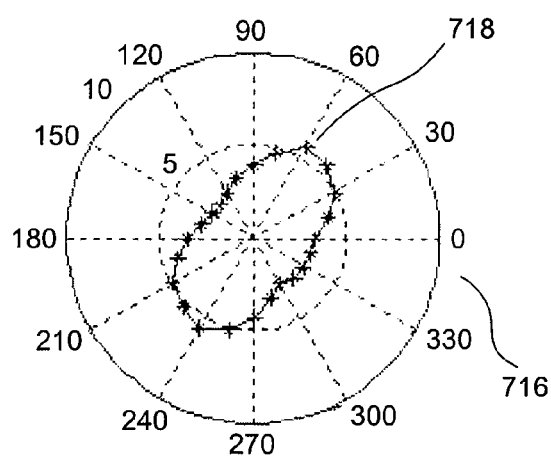
FIG. 7D is a polar coordinate plot of computed shape characteristics to slicing angles, in accordance with an embodiment of the present invention.
Figure 8:
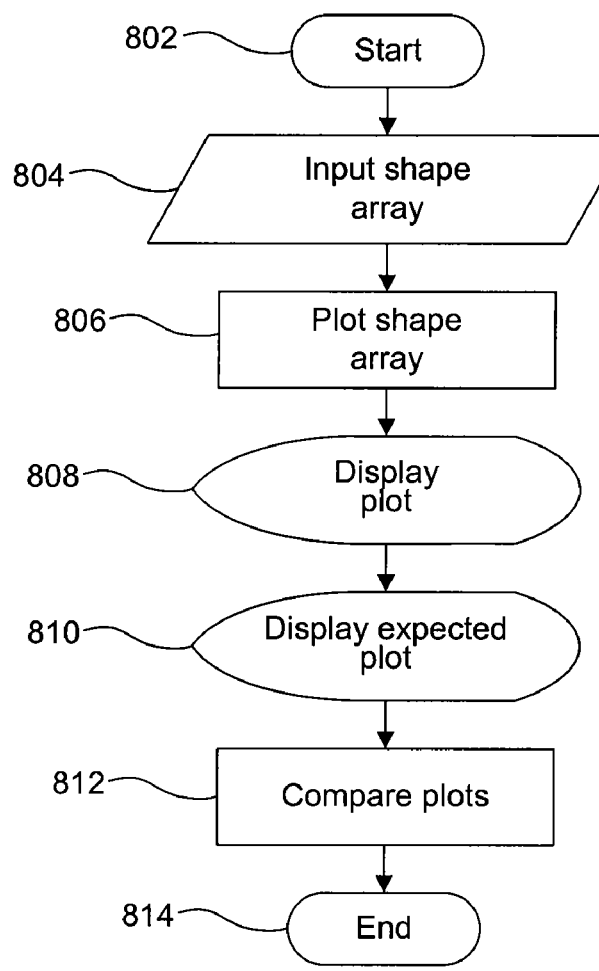
FIG. 8 is a flowchart illustrating steps by which the shape parameters computed in the flowchart of FIG. 6 are used in analyzing the event data, in accordance with an embodiment of the present invention.

A flowchart depicting a method 800 of FIG. 8 is discussed with continued reference to FIG. 7A and additional reference to FIGS. 7C and 7D. Method 800 illustrates optional steps by which the shape parameters computed in flowchart 600 of FIG. 6 are used in analyzing the event data, in accordance with an embodiment of the present invention. The method 800 starts at step 802, and proceeds to step 804, where the shape array is received as input, in accordance with an embodiment of the present invention. A number of methods exist by which data corresponding to the angles of various slicing lines and their related shape characteristics can be received by a device, module, or other entity performing the steps of method 800. Receiving this data in an array is accordingly presented by way of example, and not limitation.

At step 806, the array is plotted, in accordance with an embodiment of the present invention. The array can be plotted in various ways, and the plots 710 and 716 of FIGS. 7C and 7D, respectively, illustrate two exemplary methods through the use of an X-Y plot and a polar coordinate plot. Each plot comprises various points, each point associated with an angle 712 of the slicing line and the value of the shape characteristic for that slicing line angle, in accordance with an embodiment of the present invention. For example, point 714 of FIG. 7C corresponds to a shape characteristic between 5 and 6 (the units being irrelevant to the example, moreover considering that unitless values may be used) associated with a 60° slicing line. This is the shape characteristic value calculated using the slicing line 706 shown in FIG. 7A.

Notably, this same data can be presented in a polar coordinate plot 716 of FIG. 7D. Point 718 corresponds to a shape characteristic between 5 and 6, as with point 714 of FIG. 7C, along the associated 60° slicing line. Of interest is that, by visually comparing polar coordinate plot 716 of FIG. 7D to histogram 702 of FIG. 7A, many of the nuances of the shape of histogram 702 are reflected in the plot 716.

At step 808, the plot is displayed on a graphical display, and at step 810 an expected plot is displayed by way of comparison, in accordance with an embodiment of the present invention. This enables a medical technician to compare the two plots visually at step 812 to determine whether any significant anomalies exist. Other means of displaying the plots exist, such as through the creation of a printout as part of a patient diagnostic sheet, or by presenting a computed difference between the plot and the expected plot along certain slicing lines. The method then ends at step 814.

VI. Exemplary Advantages of Using the New Shape Parameter

Compared to the traditional methodology of calculating the standard deviation for a set of events over their associated N parameters, the new shape parameter reveals the structural or directional information of a population of events. For example, the shape parameter plotted in FIG. 7D shows that the oval population shown in the histogram of FIG. 7A has the longest span at around 60° and 240° and the shortest span at around 150° and 300°.

The new shape parameter further allows for the calculation of other shape features. For example, the oval shape illustrated in FIG. 7D is longest along the 60°-240° axis, and shortest along the 150°-330° axis. By adding the shape parameters for the 60° slice and 240° slice together, and comparing it to the sum of the shape parameters for the 150° slice and the 330° slice, the relative differences between the two lengths becomes evident.

Moreover, the pre-processing step described in Section III eliminates noise, while retaining useful information. Alternatively, this step may not be performed, however the new shape parameter results in far more statistically significant data than the traditional standard deviation methodology when noise events exist.

VII. Example Computer System Implementation

Figure 9:
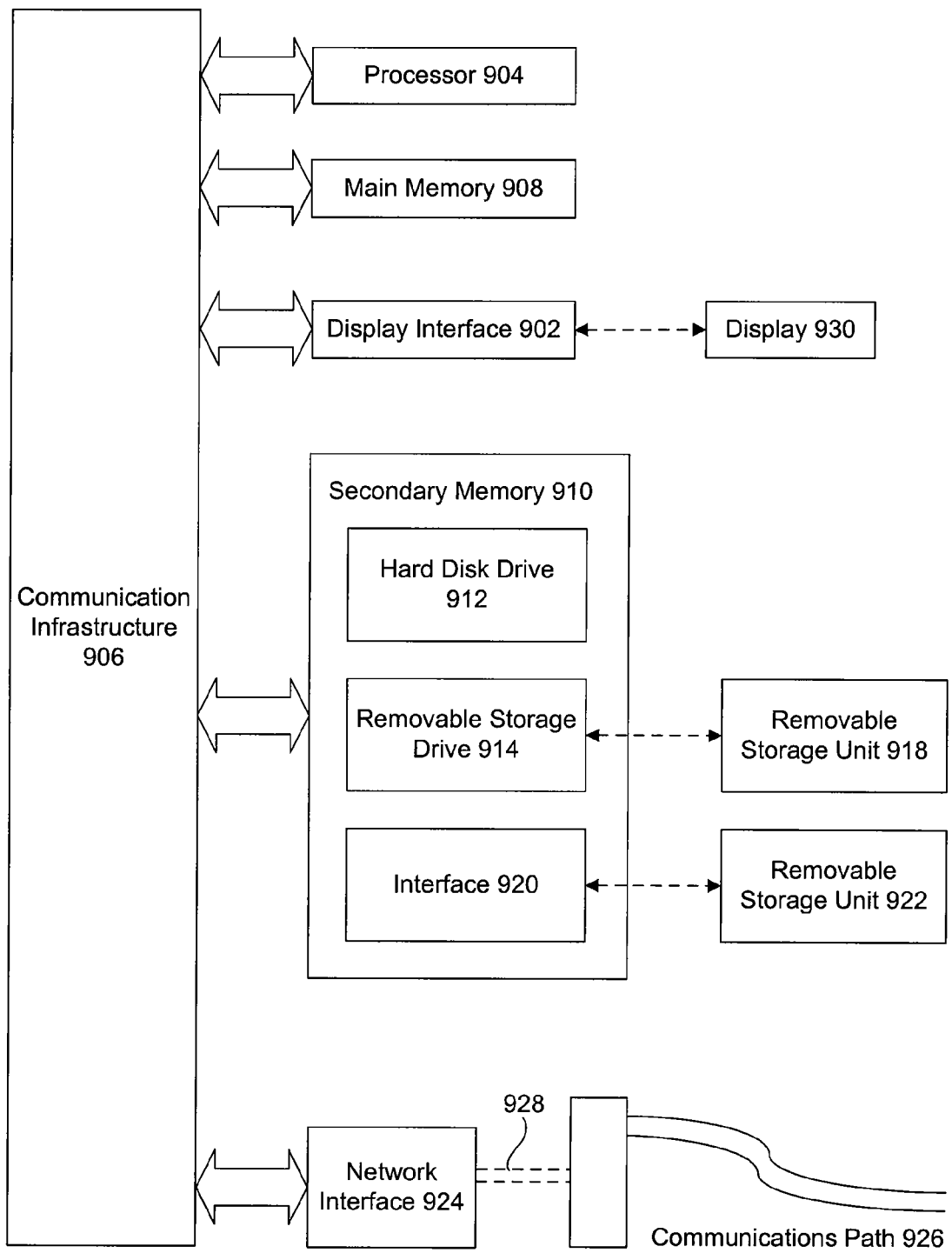
FIG. 9 depicts an example computer system in which embodiments of the present invention may be implemented.

Various aspects of the present invention can be implemented by software, firmware, hardware, or a combination thereof. FIG. 9 illustrates an example computer system 900 in which the present invention, or portions thereof, can be implemented as computer-readable code. For example, the methods illustrated by flowcharts 200 of FIG. 2, 400 of FIG. 4, 600 of FIG. 6, and 800 of FIG. 8, can be implemented in system 900. Various embodiments of the invention are described in terms of this example computer system 900. After reading this description, it will become apparent to a person skilled in the relevant art how to implement the invention using other computer systems and/or computer architectures.

Computer system 900 includes one or more processors, such as processor 904. Processor 904 can be a special purpose or a general purpose processor. Processor 904 is connected to a communication infrastructure 906 (for example, a bus or network). Computer system 900 also includes a display 930 which is connected to the communication infrastructure 906 via a display interface 902.

Computer system 900 also includes a main memory 908, preferably random access memory (RAM), and may also include a secondary memory 910. Secondary memory 910 may include, for example, a hard disk drive 912, a removable storage drive 914, and/or a memory stick. Removable storage drive 914 may comprise a floppy disk drive, a magnetic tape drive, an optical disk drive, a flash memory, or the like. The removable storage drive 914 reads from and/or writes to a removable storage unit 918 in a well known manner. Removable storage unit 918 may comprise a floppy disk, magnetic tape, optical disk, etc. which is read by and written to by removable storage drive 914. As will be appreciated by persons skilled in the relevant art(s), removable storage unit 918 includes a computer usable storage medium having stored therein computer software and/or data.

In alternative implementations, secondary memory 910 may include other similar means for allowing computer programs or other instructions to be loaded into computer system 900. Such means may include, for example, a removable storage unit 922 and an interface 920. Examples of such means may include a program cartridge and cartridge interface (such as that found in video game devices), a removable memory chip (such as an EPROM, or PROM) and associated socket, and other removable storage units 922 and interfaces 920 which allow software and data to be transferred from the removable storage unit 922 to computer system 900.

Computer system 900 may also include a communications interface 924. Communications interface 924 allows software and data to be transferred between computer system 900 and external devices. Communications interface 924 may include a modem, a network interface (such as an Ethernet card), a communications port, a PCMCIA slot and card, or the like. Software and data transferred via communications interface 924 are in the form of signals which may be electronic, electromagnetic, optical, or other signals capable of being received by communications interface 924. These signals are provided to communications interface 924 via a communications path 926 through an interconnection 928. Communications path 926 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 918, removable storage unit 922, and a hard disk installed in hard disk drive 912. Signals carried over communications path 926 can also embody the logic described herein. Computer program medium and computer usable medium can also refer to memories, such as main memory 908 and secondary memory 910, which can be memory semiconductors (e.g. DRAMs, etc.). These computer program products are means for providing software to computer system 900.

Computer programs (also called computer control logic) are stored in main memory 908 and/or secondary memory 910. Computer programs may also be received via communications interface 924. Such computer programs, when executed, enable computer system 900 to implement the present invention as discussed herein. In particular, the computer programs, when executed, enable processor 904 to implement the processes of the present invention, such as the steps in the methods illustrated by flowcharts 200 of FIG. 2, 400 of FIG. 4, 600 of FIG. 6, and 800 of FIG. 8, discussed above. Accordingly, such computer programs represent controllers of the computer system 900. Where the invention is implemented using software, the software may be stored in a computer program product and loaded into computer system 900 using removable storage drive 914, interface 920, hard drive 912 or communications interface 924.

The invention is also directed to computer program products comprising software stored on any computer useable medium. Such software, when executed in one or more data processing device, causes a data processing device(s) to operate as described herein. Embodiments of the invention employ any computer useable or readable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.).

While various embodiments of the present invention have been described above, it should be understood that they have been presented by way of example only, and not limitation. It will be understood by those skilled in the relevant art(s) that various changes in form and details may be made therein without departing from the spirit and scope of the invention as defined in the appended claims. It should be understood that the invention is not limited to these examples. The invention is applicable to any elements operating as described herein. Accordingly, the breadth and scope of the present invention should not be limited by any of the above-described exemplary embodiments, but should be defined only in accordance with the following claims and their equivalents.

What is claimed is:

1. A method for describing characteristics of a data sample, the method comprising:
   generating a multi-dimensional histogram from data representative of a plurality of physical measurement parameters on a detected object;
   determining a central portion of the histogram; and
   computing a shape parameter for the histogram along a slicing line originating at the central portion;
   wherein generating a multi-dimensional histogram, determining the central portion of the histogram, computing the shape parameter for the histogram, or any combination thereof is implemented using a programmed computer system.

2. The method of claim 1, wherein the histogram is an N-dimensional histogram corresponding to N physical measurements, where N is greater than 1.

3. The method of claim 1, further comprising: repeating the computing for additional slicing lines having additional angles, wherein the additional angles are uniformly distributed in $2\pi$ range.

4. The method of claim 1, wherein implementation using a computer system is by software, firmware, hardware, or a combination thereof.

5. The method of claim 1, further comprising: storing the shape parameter in an array such that the shape parameter is associated with an angle of the slicing line.

6. The method of claim 5, further comprising: plotting the shape parameter against the angle of the slicing line.

7. The method of claim 1, wherein the detected object is one of a population of objects.

8. The method of claim 7, wherein the population of objects is a population of blood cells.

9. The method of claim 1, wherein the computing comprises:
   interpolating frequency values for the histogram along the slicing line; and
   calculating the shape parameter using the interpolated frequency values.

10. The method of claim 9, wherein the shape parameter comprises the mean of the interpolated frequency values.

11. The method of claim 9, wherein the shape parameter comprises a distance along the slicing line at which the interpolated frequency values are below a shape parameter threshold level.

12. The method of claim 1, further comprising: removing a portion of the histogram having a characteristic below a first threshold value.

13. The method of claim 12, wherein the characteristic comprises an area of the portion of the histogram.

14. The method of claim 12, wherein the characteristic comprises a frequency of the portion of the histogram.

15. The method of claim 12, wherein the portion is a noise portion of the histogram.

16. The method of claim 12, further comprising: smoothing a remaining portion of the histogram through removing an additional portion of the remaining portion having a characteristic below a second threshold value.

17. The method of claim 16, wherein the additional portion is a noise portion of the histogram.

18. The method of claim 16, wherein the smoothing comprises convolving the remaining portion with a smoothing kernel.

19. The method of claim 18, wherein the smoothing kernel is a Gaussian kernel.

20. A system for describing characteristics of a data sample, comprising:
   generating module to generate a histogram from data representative of physical measurements on a detected object;
   determining module to determine a central portion of the histogram; and
   computing module to compute a shape parameter for the histogram along a slicing line originating at the central portion;
   wherein generating module, determining module, computing module, or any combination thereof is implemented using a programmed computer system.

21. The method of claim 20, wherein implementation using a computer system is by software, firmware, hardware, or a combination thereof.

22. A computer program product comprising a computer-usable medium having computer program logic recorded thereon that, when executed by a processor, causes the processor to describe characteristics of a data sample, the computer program logic comprising:

generating module configured to enable the processor to generate a histogram from data representative of physical measurements on a detected object;

determining module configured to enable the processor to determine a central portion of the histogram; and computing module configured to enable the processor to compute a shape parameter for the histogram along a slicing line originating at the central portion.

23. A computer-readable storage medium having computer program code recorded thereon that, when executed by a processor, causes the processor to perform a method for describing characteristics of a data sample, the method comprising:

generating a histogram from data representative of physical measurements on a detected object;

determining a central portion of the histogram; and computing a shape parameter for the histogram along a slicing line originating at the central portion.

24. A method for describing characteristics of a population of blood cells, comprising:

acquiring a blood cell from the population of blood cells in an instrument aperture;

obtaining data representative of two physical measurements for the blood cell;

determining a population type of the population based on the data;

generating a two-dimensional histogram from data, wherein the data is aggregated with additional data corresponding to the population to generate the histogram;

determining a central portion of the histogram; and computing a shape parameter for the histogram along a slicing line originating at the central portion;

wherein acquiring the blood sample, obtaining data, determining the population type, generating a two-dimensional histogram, determining the central portion of the histogram, computing the shape parameter for the histogram, or any combination thereof is implemented using a programmed computer system.

25. The method of claim 24, wherein implementation using a computer system is by software, firmware, hardware, or a combination thereof.

26. A method for detecting irregularities in a biological sample, comprising:

generating a histogram from data representative of physical measurements on the biological sample;

determining a central portion of the histogram;

interpolating frequency values for the histogram along a slicing line originating at the central portion;

calculating the shape parameter using the interpolated frequency values;

creating a plot of the shape parameter against an angle of the slicing line; and comparing the plot to an expected plot;

wherein generating the histogram, determining the central point of the histogram, interpolating frequency values for the histogram, calculating the shape parameter, creating a plot of the shape parameter, comparing the plot to the expected plot, or any combination thereof is implemented using a programmed computer system.

27. The method of claim 26, wherein implementation using a computer system is by software, firmware, hardware, or a combination thereof.

28. A particle analyzer system comprising:

a flow chamber;

a detector configured to generate electronic signals responsive to particles passing through the flow chamber;

a receiver configured to receive the electrical signals and to convert the electrical signals to captured data; and a data processor, comprising:

a generating module to generate a histogram from the captured data;

a removing module to remove a portion of the histogram having a characteristic below a first threshold value;

a smoothing module to smooth a remaining portion of the histogram through removing an additional portion of the remaining portion having a characteristic below a second threshold value;

a determining module to determine a central portion of the histogram; and a computing module to compute a shape parameter for the histogram along a slicing line originating at the central portion; and a display configured to display a plot of the shape parameter against an angle of the slicing line.

29. The system of claim 28, wherein the detector comprises a DC resistance aperture, the detector configured to measure a resistance of the DC resistance aperture and to generate the electronic signals based on the measured resistance.

30. The system of claim 28, wherein the detector comprises a light source configured to form a beam of light directed at the flow chamber, the detector configured to detect scattered photons scattered from particles passing through the flow chamber, and to generate the electronic signals based on the detected scattered photons.

31. The system of claim 28, wherein the detector comprises a light source configured to form a beam of light directed at the flow chamber, the detector configured to detect emitted photons released from excited fluorochrome and to generate the electronic signals based on the detected emitted photons.

32. The system of claim 28, wherein the detector comprises an RF conductivity aperture, the detector configured to measure conductivity of the RF conductivity aperture and to generate the electronic signals based on the measured conductivity.

* * * * *